United States Patent [19]

Cheung

[11] Patent Number: 5,028,135
[45] Date of Patent: Jul. 2, 1991

[54] COMBINED HIGH SPATIAL RESOLUTION AND HIGH TOTAL INTENSITY SELECTION OPTICAL TRAIN FOR LASER SPECTROSCOPY

[75] Inventor: H. Michael Cheung, Boston Heights, Ohio

[73] Assignee: University of Akron, Akron, Ohio

[21] Appl. No.: 403,096

[22] Filed: Sep. 5, 1989

[51] Int. Cl.$^5$ ............................................. G01N 21/00
[52] U.S. Cl. ................................... 356/340; 356/338; 350/245
[58] Field of Search .............................. 356/335–343; 250/564, 565, 524; 350/245–248, 251, 254, 256, 257

[56] References Cited
U.S. PATENT DOCUMENTS 4,176,960  12/1979  Eckbreth et al. ................ 356/338
4,242,194  12/1980  Steiner et al. ................... 204/299 R
4,676,641  6/1987   Bott ................................. 356/336
4,764,013  8/1988   Johnston .......................... 356/340

Primary Examiner—Richard A. Rosenberger
Assistant Examiner—Hoa Pham
Attorney, Agent, or Firm—Oldham & Oldham, Co.

[57] ABSTRACT

An improved method of collecting quasi-elastic light scattering (also known as QELS) data and time-average intensity simultaneously is disclosed, as is a novel apparatus therefor. The apparatus utilizes a pair of matched novel optical elements that eliminate the need of index matching fluids that are currently required to eliminate flare from the sample cell walls at the cell-sample and the cell-air interfaces. The novel optical element incorporates desirable aspects of a pinhole aperture optical system and a double lens and center mask optical system.

16 Claims, 3 Drawing Sheets

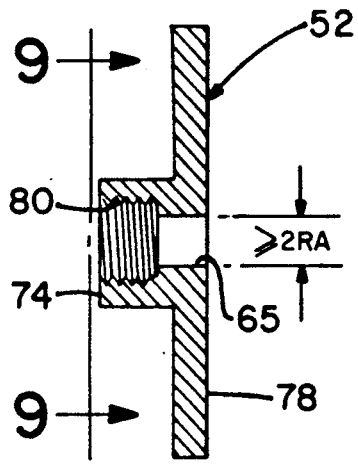
FIG.-8
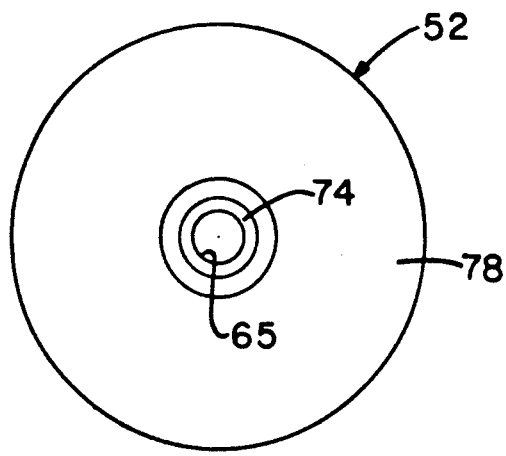
FIG.-9
FIG.-10
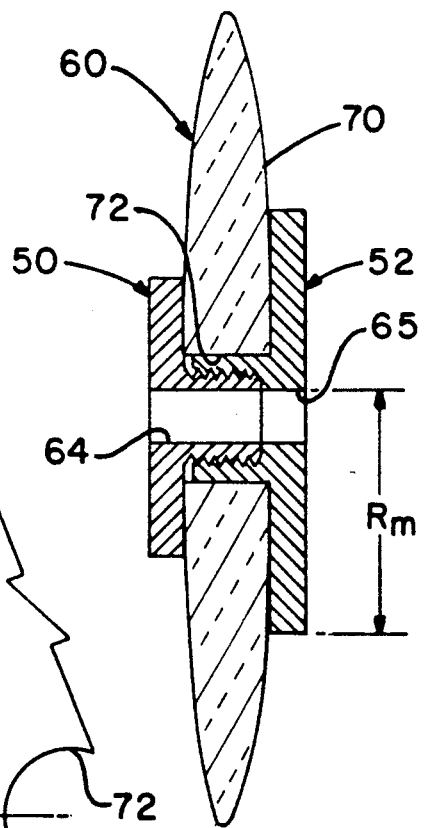
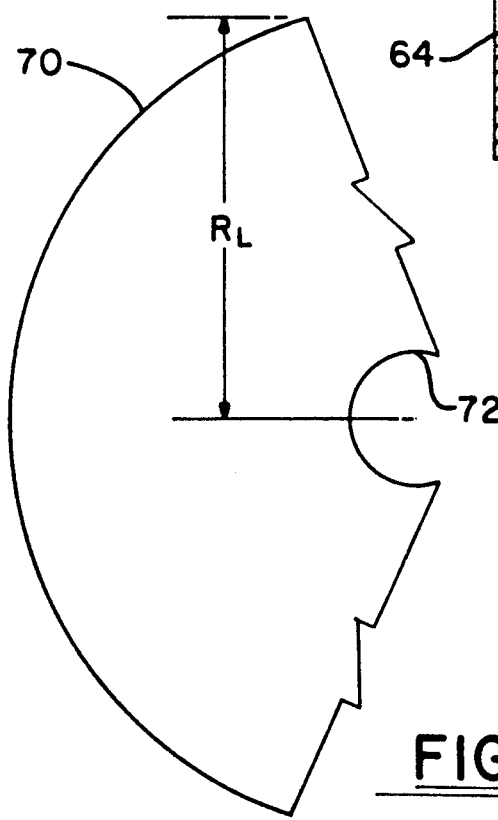
FIG.-11
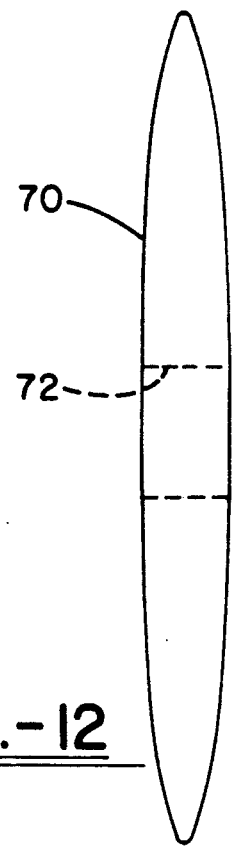
FIG.-12

COMBINED HIGH SPATIAL RESOLUTION AND HIGH TOTAL INTENSITY SELECTION OPTICAL TRAIN FOR LASER SPECTROSCOPY

The present invention relates to an improved method of collecting quasi-elastic light scattering (also known as QELS) data and an apparatus therefor. More specifically, it relates to a method of increasing the spatial resolution obtained by utilizing a pair of novel optical elements for collecting these data. Even more specifically, it relates to a novel optical element that eliminates the need of index matching fluids that are currently required to eliminate flare from the sample cell walls at the cell-sample and the cell-air interfaces.

DISCUSSION OF THE BACKGROUND ART

Light scattering experiments, particularly laser light scattering experiments, are commonly employed for measuring properties of certain physical systems such as solutions, microemulsions, micellar solutions, and colloidal dispersions. One common goal is to obtain data such as particle size, based upon diffusion coefficients. In measuring the scattering of laser light from such a physical system, it is important to measure not only the total (also referred to as "time-average" or "K-vector") intensity of the light scattered at a given fixed angle $\theta$, but it is also important to measure the intensity fluctuations of the light with time. The object of this invention and, indeed, other research, is to provide a single apparatus that can simultaneously attain both pieces of data.

The difficulty encountered in making both measurements simultaneously is that the gathering of total intensity data requires a very precise determination of the angle of scattering $\theta$, while the accurate collection of the intensity fluctuation data requires only a ralatively accurate determination of $\theta$, but requires a very precise determination of the spatial resolution, that is, knowing exactly where in the sample plane the measurement is being made. This requirement for nigh spatial resolution arises from the fact that the observed intensity fluctuations observed arise from two different sources. The first source is called "homodyning" and is the interaction or interference caused by the scattering of light from separate particles in the physical system. This effect is the effect of interest to the researcher. The second source of fluctuations is called "heterodyning". It arises from light scattering at the wall of the sample holder, both at the wall-air interface and the wall-sample interface. Even a small error due to heterodyning can grossly affect the results in measuring fluctuation, although the net effect upon total intensity results is minimal.

The commonly accepted method of eliminating heterodyning effects is to immerse the sample cell in a liquid that has the same refractive index as the sample cell itself. This is referred to as use of an indexmatching fluid. When the sample cell is constructed of glass, which is the most common case, the liquid of choice is toluene, which has recently come under intense scrutiny due to detrimental health effects. These effects are especially intolerable in a closed environment, as one would encounter in a space vehicle such as the space shuttle. Therefore, a method for obtaining the two distinct measures simultaneously using a single apparatus and not requiring a liquid such as toluene would be extremely beneficial for use in space applications.

A second, and not as common, method of eliminating heterodyning effects on the wall surfaces is to place an opaque mask in the middle portion of the optical train between two lenses used to focus and then refocus the image. Using such masks creates "dead zones" in the image which can be used to eliminate scattering from the walls of the sample cell. Although opaque masks are very effective when used in the center portion of the lens train, the best data point for collecting total intensity, that is, the line of light that passes directly through the middle of each lens, becomes, unfortunately, unavailable, since it has been blocked by the opaque mask.

Another method of obtaining both pieces of data, that is, both total and fluctuation intensities, without use of an index matching fluid, is to use two separate optical trains. The obvious disadvantage to the researcher in this case is that the data are not simultaneously obtained, and inaccuracies due to changes in the light source, the sample, the angular position of the optical train, or other changes, are inevitably introduced.

SUMMARY OF THE INVENTION

A first aspect of this invention is to provide a novel optical element that can effectively mask certain light fluctuations arising from heterodyning by providing high spatial resolution without eliminating the "through the center" light data.

A second aspect of this invention is to provide a novel optical element that provides high spatial resolution without the use of index matching fluids, particularly hazardous liquids such as toluene.

A third aspect of this invention is to provide a single optical train employing a pair of the matched optical elements capable of collecting both total and fluctuation light intensities from a sample cell simultaneously.

A fourth aspect of this invention is to provide an optical system that can achieve the above objective without use of index matching fluids such as toluene.

A fifth aspect of this invention is to provide a method for simultaneously collecting total and fluctuation light data by use of a single optical train utilizing a pair of novel optical elements and without the use of index matching fluids.

These and other aspects of the invention are achieved by a novel optical element specially adapted for simultaneously acquiring scattered light data, said optical element comprising: a lens, having first and second faces, a focal length f, and having a hole bored concentrically therethrough from the first face to the second face; and first and second lens insert elements; said first lens insert element comprising an essentially hollow cylinder having first and second ends, said cylinder having an external diameter slightly smaller than the diameter of the hole in the lens and an internal surface with an engaging means disposed on at least a portion thereof, and a flanged portion affixed perpendicular to the external surface of the solid near the second end, said flanged portion having a diameter no larger than 2 RL, where RL is the radius of the lens; said second lens insert element comprising an essentially solid cylinder having first and second ends with a hole of diameter 2 RA bored centrally longitudinally therethrough, where RA is the desired aperture radius for the optical element, said cylinder having an external surface with an engaging means disposed thereon, adapted for engaging the internal surface of the first lens insert element, and a flanged portion affixed perpendicular to the external surface of the solid near the second end: said first and second lens insert elements having lengths such that when the first end of the first lens insert element is disposed into the hole in the lens from the first face of the lens and the first end of the second lens insert element is inserted into the first end of the first lens insert element and the engaging means thereon is engaged by the engaging means on the first lens insert element, the respective flanged portions of the first and second lens insert elements bear slightly upon the respective first and second faces of the lens.

Further or these aspects are achieved by an optical train utilizing a pair of the novel optical elements, said train being disposed upon a base of conventional design that is adapted to move smoothly in an arc coplanar to the scattered light beam and receive the light beam along a longitudinal axis thereof, said train comprising a first optical element being the novel optical element cited above; a second optical element, also being the novel optical element cited above, wherein the lens has the same focal length f and the same radius RL as the lens of the first optical element; an aperture element, said aperture element being essentially an opaque plate with an aperture of diameter 2 RA bored perpendicularly therethrough; first and second light detecting means; and first and second light analyzing means; said first optical element, second optical element, first light detecting means, aperture element and second light detecting means being disposed colinearly, in that order, upon the base along the axis of the scattered light beam, such that each is centered upon the light beam, the first optical element being located one focal length f from the center of the sample cell, the first light detecting means being proximate to the second optical element, the aperture element being located one focal length f from the second optical element, and the second light detecting means being proximate to the aperture element; said first and second light detecting means communicated to first and second light analyzing means by conventional electrical wiring means, irrelevant of whether said first and second analyzing means are disposed upon said base.

Even further aspects of this invention are achieved by a method for simultaneously acquiring total intensity and fluctuation light scattering data, said method comprising: causing a light beam to be emitted from a light source and to pass into a sample contained within a sample cell, wherein certain portions of the incident light beam are scattered; aligning an optical train, as described above and having first and second light detecting means, at a fixed angle $\theta$ from the incident axis of said light beam; collecting simultaneously total intensity light data in the first light detecting means and fluctuation light data in the second light detecting means; communicating simultaneously said total intensity light data and said fluctuation light data via conventional electrical wiring means to respective first and second light analyzing means; and analyzing simultaneously said total intensity light data and said fluctuation light data in respective first and second light analyzing means.

BRIEF DESCRIPTION OF THE DRAWINGS

FIG. 8 is a cross-section view of the second lens insert element of the present invention.

FIG. 9 is a top view of the second lens insert element to the present invention.

FIG. 10 is a cross-section view of the first and second lens insert elements of the present invention, as engaged with a lens to form the novel optical element.

FIG. 11 is a plan view of a portion of the modified lens used to construct the novel optical element of the invention.

FIG. 12 is a side view of the modified lens used to construct the novel optical element of the invention.

DETAILED DESCRIPTION OF THE DRAWINGS

Figure 1:
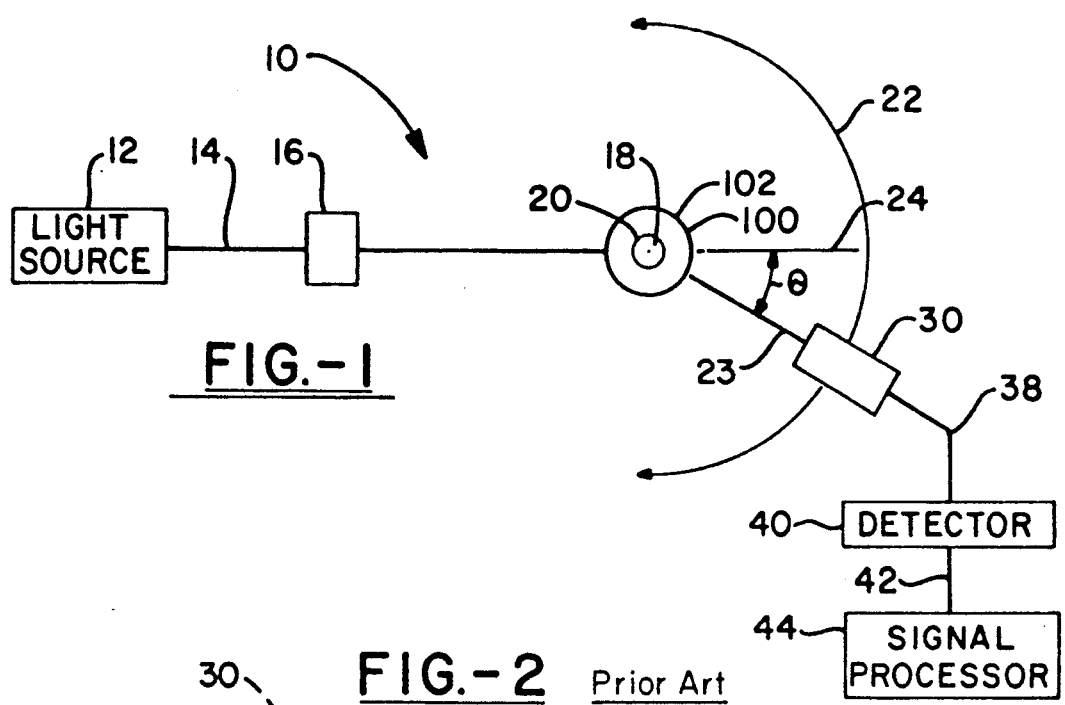
FIG. 1 is a general drawing of the apparatus used in light scattering spectroscopy, indicating the position of the optical train of this invention therein.

FIG. 1 shows the general layout of the optical apparatus 10 used to collect light scattering data from a sample 18, most commonly a liquid sample containing a physical system such as a polymer solution, a microemulsion, a micellar solution or a colloidal suspension, contained within a sample cell 20. A light beam 14 is generated by a light source 12, preferably a source of monochromatic and coherent light, such as obtained from a laser of the sort conventionally available. The light beam 14 may be passed through a conditioning train 16, wherein the beam is collimated, polarized, or otherwise conditioned for passage through the sample cell 20. Conditioning means of this sort are well known and obvious to those skilled in this art.

An optical train 30, the exact details of which are disclosed later, but which generally contains means for conditioning and receiving a scattered light beam 23 of the sort as light beam 14, is disposed at an angle $\theta$ from the incident axis 24 of the light beam, although the optical train 30 is disposed so as to be able to pivot along a planar arc 22 about the center of the sample so that the angle $\theta$ may be varied from 0° to almost 180°, although it will be readily apparent that the approach to an angle of 180° will be limited by the size of the optical train 30 and its interference with the incident light beam 14.

Optical train 30 is connected by conventional electrical means 8 to analyzing means 40, which is sequentially connected by conventional electrical means 42 to a signal processing means 44. In this manner, which is well known in the art, the intensity of the scattered light beam 23 may be measured and recorded.

In one known method for obtaining the desired fluctuation data, the sample cell 20 is enveloped by an optional cell 100. said optional cell containing a fluid 102 with an index of refraction close to that of the wall of sample cell 20. This method would commonly use the optical train 30 disclosed in FIG. 2 to collect the fluctuation data.

In a second known method for obtaining the desired fluctuation data, the optional cell 100 and fluid 102 are not utilized, but total intensity data and intensity fluctuation data are not collected simultaneously. The former are collected with an optical train 30 is disclosed in FIG. 2 and the latter are collected with an optical train 30 as disclosed in FIG. 3 or FIG. 4.

In the method of this invention for collecting total and fluctuation intensity data simultaneously, the optional cell 100 and fluid 102 are not used. The optical train used in method of the invention is the optical train disclosed in FIG. 5 and described further below.

Figure 2:
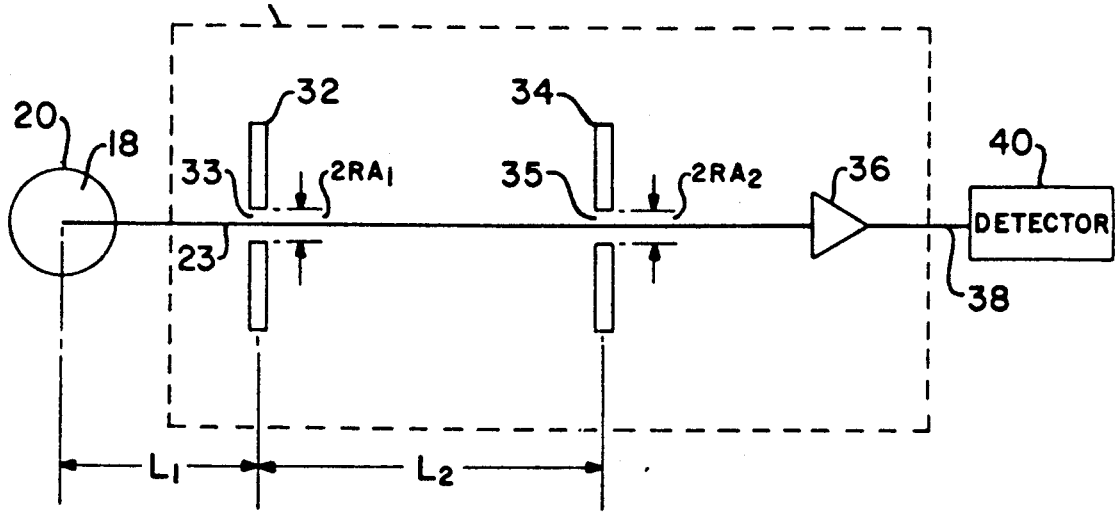
FIG. 2 is a depiction of the "double pinhole"-type of optical train of the prior art.

Referring now to FIG. 2, the "double-pinhole" type of optical train 30 is disclosed. This type of optical train is well known in the prior art. The scattered light beam 23 originates within the sample 18, which sample is contained in the sample cell 20. Optical train 30 is aligned with the scattered light beam 23 such that, at a distance $L_1$ from the origin of the scattered beam, the beam encounters a first aperture element 32. This aperture element, comprising material that is opaque to the electromagnetic energy of scattered light beam 23, has an aperture 33, of radius $RA_1$, located centrally therein. A second aperture element 34 is located colinearly along light beam 23 and at a distance $L_2$ further from the light source than first aperture element 32. Second aperture element 34, also opaque to light beam 23, has an central aperture 35, of radius $RA_2$, disposed therein. Also colinear with light beam 23 is a light detection means 36, preferably a photodiode or photomultiplier tube (PMT), either of which are conventional, and either of which are used to gather electromagnetic energy in the form of photons and convert said energy into a electrical impulse. Such an impulse can be passed via conventional electrical wiring 38 to a light analyzing means 40 for further analysis.

Such a "double-pinhole" system is ideal for providing a very exact angular resolution, since only light that originates along or very close to the light beam 23 can reach the light detection means 36, and the cross-axis resolution, which is the spatial selectivity of the optical train on an axis perpendicular to the light beam 23, can be made arbitrarily small by adjusting the sizes of $RA_1$, $RA_2$, $L_1$ and $L_2$. In fact, the double-pinhole sYstem has an angular resolution which cannot be matched by any system that contains lenses. Unfortunately, it is also abundantly obvious that any light that originates along the axis of the light beam 23 and surrounding cross-axis resolution will reach the detection means 36, so this system is said to have no "on-axis" resolution, and the data obtained are useless by themselves to eliminate the heterodyning effects of the walls.

An ideal optical train will measure total intensity by use of the "double-pinhole" method.

Figure 3:
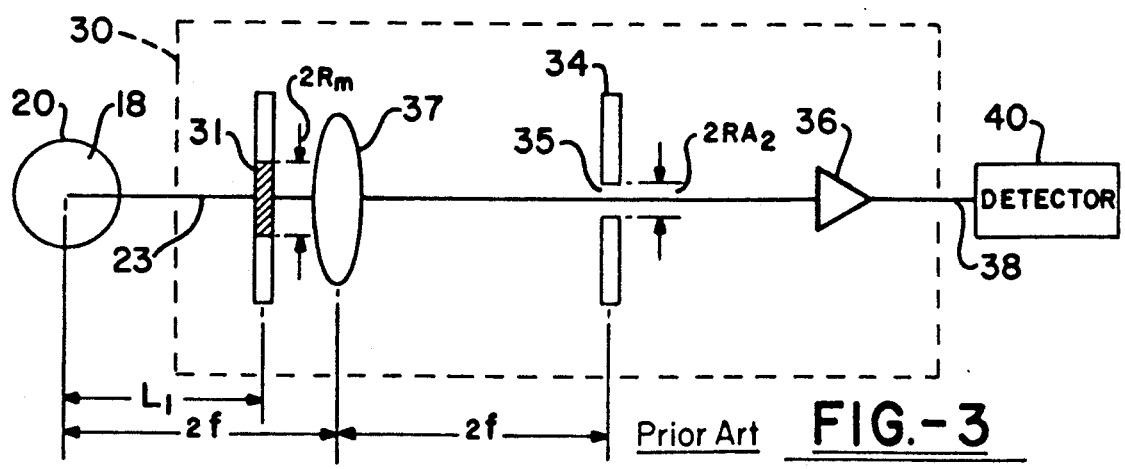
FIG. 3 is a depiction of the "single lens"-type of optical train of the prior art.

Referring now to FIG. 3, an alternate optical train, the "single-lens" system, known in the prior art is disclosed. The scattered light beam 23 originates within the sample 18, which sample is contained in the sample cell 20. optical train 30 is aligned with the scattered light beam 23 such that, at a distance $L_1$ from the origin of the scattered beam, the beam encounters an optional opaque masking element 31 of radius RM at a distance $L_1$ from the source. This masking element prevents direct passage of "on axis" light through the optical train. Certain light can, however, enter a focusing lens 37, located at a distance twice the focal length f of the lens from the source, and any such light will be focused on a point colinear with the source and at a distance two focal lengths further along the light axis 23 from the lens 37. An aperture element 34 is located colinearly along light beam 23 and such a distance 2f from the lens 37. The aperture element 34, also opaque to light beam 23, has an central aperture 35, of radius $RA_2$, disposed therein, and it serves to cut out extrinsic light not originating at the light source. Also colinear with light beam 23 is a light detection means 36, preferably a photodiode or photomultiplier tube (PMT), either of which are conventional, and either of which are used to gather electromagnetic energy in the form of photons and convert said energy into a electrical impulse. Such an impulse can be passed via conventional electrical wiring to a light analyzing means 40 for further analysis.

In terms of "on axis" resolution, the single lens system offer no improvement over the double-pinhole design if no masking element 31 is used, since no light originating along the light beam axis 23 is excluded, and, in fact, the angular resolution decreases from the double-pinhole system. But a properly selected (using conventional and well known optics principles) center mask can begin to discriminate as to "on axis" light and provide the desired spatial resolution.

Figure 4:
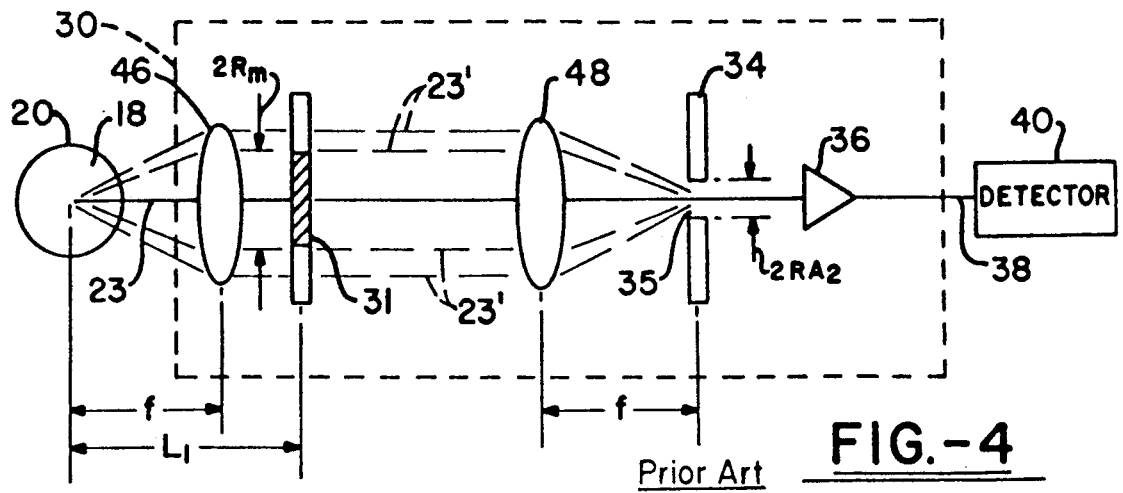
FIG. 4 is a depiction of the "double lens"-type of optical train.

Referring now to FIG. 4, another alternate optical train 30, the "double lens" system, is disclosed. As with FIG. 2 and 3, the scattered light beam 23 originates within the sample 18, which sample is contained in the sample cell 20. Optical train 30 is aligned with the scattered light beam 23 such that the light beam 23 encounters a first lens 46 at a distance one focal length from the origin of the light scattering. Elementary optics requires that such light entering the lens will not refocus of itself, and will, instead, be split into a plurality of beams 23' parallel to light axis 233. At a distance $L_1$ from the scattering source, the plurality of beams encounters an optional opaque masking element 31 of radius RM, centered on the light axis 23. This masking element will exclude all beams from lens 46 that are closer than RM to the light axis 23. A second lens 48, with an identical focal length f to that of first lens 46, and located colinear to lens 46 will refocus the plurality of beams 23' reaching it into a single point colinear with the source and at a distance one focal length f further along the light axis 23 from the lens 48. An aperture element 334 is located colinearly along light beam 23 and such a distance f from the lens 37. The aperture element 34, also opaque to light beam 23, has an central aperture 35, of radius $RA_2$, disposed therein, and it serves to cut out extrinsic light not originating at the light source. Also colinear with light beam 23 is a light detection means 36, preferably a photodiode or photomultiplier tube (PMT), either of which are conventional, and either of which are used to gather electromagnetic energy in the form of photons and convert said energy into a electrical impulse. Such an impulse can be passed via conventional electrical wiring to a light analyzing means 40 for further analysis.

This manner of optical train greatly improves the "on axis" resolution, but the angular uncertainty increases dramatically, making the double lens optical train quite undesirable for making total intensity measurements. As with the single lens system, the use of the center mask increases angular uncertainty, but the increased "on axis" spatial resolution more than compensates for the loss of angular certainty.

The optics of the dual lens system permit some optimization of the elements involved and it can be shown that the preferred mask radius RM of mask element 31 is about 0.8 RL, where RL is the radius of lenses 46 and 48.

Figure 5:
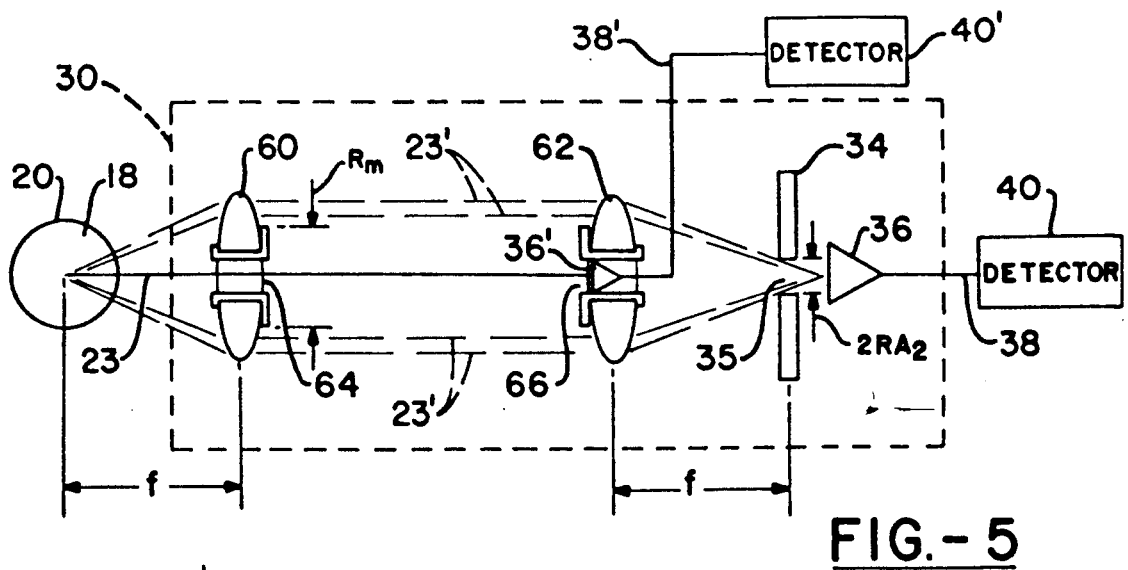
FIG. 5 is a depiction of the optical train of the present invention.

The optical train of the present invention is disclosed now in FIG. 5. The present invention incorporates the best elements of the double pinhole system with those of the dual lens system so as to allow simultaneous acquisition of total intensity data via the preferred double pinhole method and fluctuation data via the preferred dual lens method. In this manner, the prior art's need for indexing fluid is eliminated and a compact dual purpose optical train is facilitated.

As in the prior figures, the scattered light beam 23 originates within the sample 18, which sample is contained in the sample cell 20. Optical train 30 is aligned with the scattered light beam 23 such that the light beam 23 encounters a first combined optical element 60 at a distance one focal length from the origin of the light scattering. The construction of this combined optical element 60 is described in more detail below, but suffice it to say for now that the combined optical element incorporates desirable aspects of a pinhole aperture, a lens and a mask element of radius RM, that the pinhole aperture 64 is aligned with the light beam 23 and that the mask element is positioned opposite the incident scattered light beam 23. Elementary optics requires that such light entering the lens aspect will not refocus of itself, and will, instead, be split into a plurality of beams 23' parallel to light axis 23. At a distance L from the scattering source, the plurality of beams 23' created by the lens aspect encounters a second combined optical element 62, the masking component of which, being disposed on the front face of the second combined optical element 62 and having radius RM centered on the light axis 23, excludes all beams from lens 46 that are closer than RM to the light axis 23. The lens aspect of the second combined optical element, having an identical radius RL and focal length f to that of the lens aspect of the first combined optical element 60 and being located colinear to the lens aspect of the first combined optical element will refocus the plurality of beams 23' reaching it into a single point colinear with the source and at a distance one focal length f further along the light axis 23 from the second combined optical element 62. An aperture element 34 is located colinearly along light beam 23 and such a distance f from the second combined optical element 62. The aperture element 34, also opaque to light beam 23, has an central aperture 35, of radius $RA_2$, disposed therein, and it serves to cut out extrinsic light not originating at the light source. Also colinear with light beam 23 is a first light detection means 36, preferably a photodiode or photomultiplier tube (PMT), either of which are conventional, and either of which are used to gather electromagnetic energy in the form of photons and convert said energy into a electrical impulse. Such an impulse can be passed via a first conventional electrical wiring means 38 to a first light analyzing means 40 for further analysis.

The optical train of the present invention offers, however, an alternative light path. The pinhole aspect 64 of the first combined optical element 60 permits light encountering it along the light beam axis 23 to pass directly through the optical element, as in the conventional pinhole aperture disclosed in FIG. 2. At a distance L from the first combined optical element 60, this light encounters the pinhole aspect 66 of the second combined optical element 62, which is colinear to the first combined optical element 60. Directly within the pinhole aspect 66 the light strikes a second light detection means 36', preferably a photodiode or photomultiplier tube (PMT), either of which are conventional, and either of which are used to gather electromagnetic energy in the form of photons and convert said energy into a electrical impulse. Such an impulse can be passed via a second conventional electrical wiring means 38' to a second light analyzing means 40' for further analysis.

Once collected, the data from the first light analyzing means 40 are analyzed for the fluctuation characteristics of the sample and the data from the second light analyzing means 40' are analyzed for the total intensity characteristics of the sample. In this manner, simultaneous data acquisition is achieved.

FIGS. 6 through 12 reveal more descriptively the elements of the combined optical element of the present invention.

FIG. 11 shows a plan view of a portion of a focusing lens 70 of the sort well known in the art, having focal length f and radius RL. FIG. 12 shows a side view of the same lens. The lens 70 may be any sort of focusing lens, including convex-convex, plano-convex, achromatic, aspheric, or the like. A hole 72, small in diameter relative to lens radius RL but larger than twice the desired pinhole aperture RA is bored concentrically into the lens 70 by known conventional means.

As illustrated best in FIGS. 8 and 9, a first lens insert element 52 is prepared from a rigid material, opaque to light 23 of the sort used in the optical train 30 Preferably this material is metallic, but the exact selection of material will be obvious to one skilled in this art. The first lens insert element 52 is essentially a cylindrical solid having first and second ends 74 and 76, respectively, with a circular flanged portion 78 at the second end 76 thereof. The cylindrical portion of the first lens insert element 52 has an external diameter slightly smaller than the diameter of the hole 72 bored concentrically into the lens 70, thereby providing a close fit between the lens and the insert element. Starting at the first end 74 of the cylindrical portion, at least a significant part of the internal surface 80 of the cylindrical portion is adapted for engaging, preferably threadingly, the external surface of a second lens insert element, although it is not necessary that the threading extend the entire length thereof. The unthreaded portion of the internal surface, if any, has a diameter no smaller than 2 RA, the desired aperture radius for the aperture function which this element will perform. The circular flanged portion 78 is to function as the masking element, so it has a radius RM, and, in the preferred embodiment, this radius RM is sized to be about 0.8 RL, where RL is the radius of the lens wherein the insert element will be fitted.

Figures 6, 7:
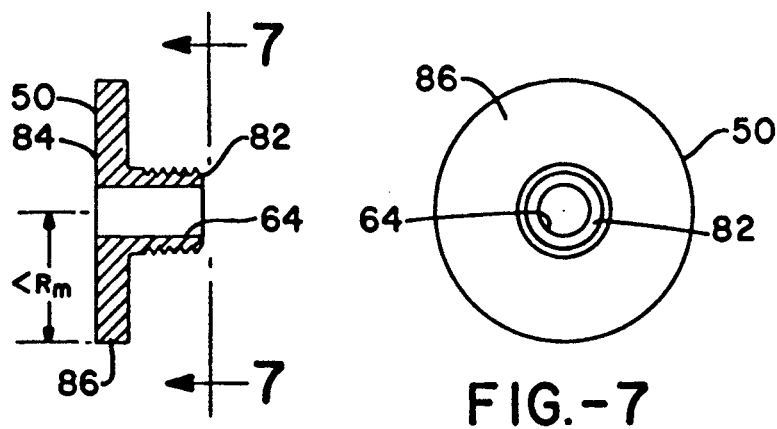
FIG. 6 is a cross-section view of the first lens insert element of the present invention.
FIG. 7 is a top view of the first lens insert element of the present invention.

As illustrated best in FIGS. 6 and 7, a second lens insert element 50 is also prepared from a rigid material, opaque to light 23 of the sort used in the optical train 30. This element should be manufactured from the same material as the first lens insert element 52. Preferably this material is metallic, but the exact selection of material will be obvious to one skilled in this art. The second lens insert element 50 is essentially a cylindrical solid having first and second ends, 82 and 84, respectively, with a circular flanged portion 86 at the second end 84 thereof. The cylindrical portion of the lens insert element 52 has an external diameter sized and adapted, for at least a portion of its length, beginning at its first end 82, to engage, preferably threadingly, the internal surface 80 of the first lens insert element 50. The internal diameter of the cylindrical portion is 2 RA, as this opening 64 will function as the pinhole aperture in the combined optical element. The circular flanged portion 86 at the second end 84 of the cylindrical portion does not perform a masking function, so the radius of the flanged portion is not generally critical to the invention, but the flanged portion should have a radius no larger than RM and the flanged portion 86 should extend far enough beyond the cylindrical portion to secure and support the lens wherein the insert elements will be fitted.

As best shown in FIG. 10, when the first and second lens insert elements, 52 and 50, respectively, are engaged with each other by engaging their respective first ends 74 and 82 from opposite sides of the hole 72 bored in lens 70, the first and second insert elements 52 and 50 should engage each other enough that the flanged portions of each, 78 and 86, respectively, should closely approach the external surface of the lens 70, and slightly bear upon it.

Thus constructed, the lens 70 with lens insert elements 52 and 50 properly engaged therein constitutes the novel optical element of this invention that is illustrated as 60 and 62 in FIG. 5. When utilized in the configuration illustrated therein and described herein, the objects of the invention are achieved.

While in accordance with patent statutes, a preferred embodiment and best mode have been presented, the scope of the invention is not limited thereto, but rather is measured by the scope of the attached claims.

I claim:

1. An optical assembly having a central aperture of radius RA specially adapted for simultaneously acquiring scattered light data, said optical assembly comprising:
    a focusing lens, having first and second faces, a focal length f, a radius RL, and having a hole bored concentrically therethrough from the first face to the second face; and
    first and second lens insert elements;
    said first lens insert element comprising an essentially hollow cylinder having first and second ends, said cylinder having an external diameter slightly smaller than the diameter of the hole in the lens and an internal surface with an engaging means disposed on at least a portion thereof, and a flanged portion affixed perpendicular to the external surface of the cylinder near the second end, said flanged portion having a diameter no larger than 2 RL;
    said second lens insert element comprising an essentially solid cylinder having first and second ends with a hole of diameter 2 RA bored longitudinally therethrough, said cylinder having an external surface with an engaging means disposed thereon, adapted for engaging the internal surface of the first lens insert element, and a flanged portion affixed perpendicular to the external surface of the cylinder near the second end;
    said first and second lens insert elements having lengths such that when the first end of the first lens insert element is disposed into the hole in the lens from the first face of the lens and the first end of the second lens insert element is inserted into the first end of the first lens insert element and the engaging means thereon is engaged by the engaging means on the first lens insert element, the respective flanged portions of the first and second lens insert elements bear slightly upon the respective first and second faces of the lens.

2. The optical assembly of claim 1 wherein the engaging means is provided by threading.

3. The optical element of claim 1 wherein the first and second lens insert elements are composed of a material that is opaque to the light to be detected.

4. The optical element of claim 1 wherein the flanged portion of the first optical insert element has a diameter of 1.6 RL.

5. The optical assembly of claim 1 wherein the lens is convex-convex.

6. The optical assembly of claim 1 wherein the lens is plano-convex.

7. The optical assembly of claim 1 wherein the lens is achromatic.

8. The optical assembly of claim 1 wherein the lens is aspheric.

9. An optical train for simultaneously measuring the intensity and fluctuations of a light beam scattered by a sample contained in a sample cell, said train being disposed upon a base to move smoothly in an arc coplanar to the scattered light beam and receive the light beam along a longitudinal axis thereof, said train comprising:
    a first optical assembly having a central aperture of radius RA, and a focusing lens element with radius RL and focal length f, said optical assembly being specially adapted for simultaneously acquiring scattered light data;
    a second optical assembly having a central aperture of radius RA and a focusing lens element with a radius RL and focal length f, said optical assembly being specially adapted for simultaneously acquiring scattered light data;
    an aperture element, said aperture element being essentially an opaque plate with an aperture of diameter 2 RA bored perpendicularly therethrough;
    first and second light detecting means; and
    first and second light analyzing means;
    said first optical assembly, second optical assembly, first light detecting means, aperture element and second light detecting means being disposed colinearly, in that order, upon the base along the axis of the scattered light beam, such that each is centered upon the light beam, the first optical assembly being located one focal length f from the center of the sample cell, the first light detecting means being proximate to the second optical assembly, the aperture element being located one focal length f from the second optical assembly, and the second light detecting means being proximate to the aperture element;
    said first and second light detecting means communicated to first and second light analyzing means by electrical wiring means, irrelevant of whether said first and second analyzing means are disposed upon said base.

10. The optical train of claim 9, wherein at least one of the first and the second light detecting means is a photomultiplier tube.

11. The optical train of claim 9, wherein at least one of the first and the second light detecting means is a photodiode.

12. The optical train of claim 9 wherein said first and second optical assemblies comprise:
    a focusing lens, having first and second faces, a focal length f, a radius RL, and having a hole bored concentrically therethrough from the first face to the second face; and
    first and second lens insert elements;
    said first lens insert element comprising an essentially hollow cylinder having first and second ends, said cylinder having an external diameter slightly smaller than the diameter of the hole in the lens and an internal surface with an engaging means disposed on at least a portion thereof, and a flanged portion affixed perpendicular to the external surface of the cylinder near the second end, said flanged portion having a diameter no larger than 2 RL;

said second lens insert element comprising an essentially solid cylinder having first and second ends with a hole of diameter 2 RA bored longitudinally therethrough, said cylinder having an external surface with an engaging means disposed thereon, adapted for engaging the internal surface of the first lens insert element, and a flanged portion affixed perpendicular to the external surface of the cylinder near the second end;

said first and second lens insert elements having lengths such that when the first end of the first lens insert element is disposed into the hole in the lens from the first face of the lens and the first end of the second lens insert element is inserted into the first end of the first lens insert element and the engaging means thereon is engaged by the engaging means on the first lens insert element, the respective flanged portions of the first and second lens insert elements bear slightly upon the respective first and second faces of the lens.

13. A method for simultaneously acquiring total intensity and fluctuation light scattering data, said method comprising:

causing a light beam to be emitted from a light source and to pass into a sample contained within a sample cell;

aligning an optical train at a fixed angle $\theta$ from the incident axis of said light beam, said optical train disposed on a base and comprising: first and second optical assemblies, each having a central aperture of radius RA, and a focusing lens element with radius RL and focal length f, each said optical assembly being specially adapted for simultaneously acquiring scattered light data; an aperture element, said aperture element being essentially an opaque plate with an aperture of diameter 2 RA bored perpendicularly therethrough; first and second light detecting means; and first and second light analyzing means; said first optical assembly, second optical assembly, first light detecting means, aperture element and second light detecting means, aperture element and second light detecting means being disposed colinearly, in that order, upon the base along the axis off the scattered light beam, such tat each is centered upon the light beam, the first optical assembly being located one focal length f from the center of the sample cell, the first light detecting means being proximate to the second optical assembly, the aperture element being located one focal length f from the second optical assembly, and the second light detecting means being proximate to the aperture element; said first and second light detecting means communicated to first and second light analyzing means by conventional electrical wiring means, irrelevant of whether said first and second analyzing means are disposed upon said base;

collecting simultaneously total intensity light data in the first light detecting means and fluctuation light data in the second light detecting means;

communicating simultaneously said total intensity light data and said fluctuation light data via conventional electrical wiring means to respective first and second light analyzing means; and analyzing simultaneously said total intensity light data and said fluctuatioon light data in respective first and second light analyzing means.

14. The method of claim 13, wherein the light source is a laser.

15. The method of claim 13, wherein no index matching fluid is used with the sample cell to eliminate wall effects.

16. The method of claim 13 wherein said first and second optical assemblies comprise:

a focusing lens, having first and second faces, a focal length f, a radius RL, and having a hole bored concentrically therethrough from the first face to the second face; and first and second lens insert elements;

said first lens insert element comprising an essentially hollow cylinder having first and second ends, said cylinder having an external diameter slightly smaller than the diameter of the hole in the lens and an internal surface with an engaging means disposed on at least a portion thereof, and a flanged portion affixed perpendicular to the external surface of the cylinder near the second end, said flanged portion having a diameter no larger than 2 RL;

said second lens insert element comprising an essentially solid cylinder having first and second ends with a hole of diameter 2 RA bored longitudinally therethrough, said cylinder having an external surface with an engaging means disposed thereon, adapted for engaging the internal surface of the first lens insert element, and a flanged portion affixed perpendicular to the external surface of the cylinder near the second end;

said first and second lens insert elements having lengths such that when the first end of the first lens insert element is disposed into the hole in the lens from the first face of the lens and the first end of the second lens insert element is inserted into the first end of the first lens insert element and the engaging means thereon is engaged by the engaging means on the first lens insert element, the respective flanged portions of the first and second lens insert elements bear slightly upon the respective first and second faces of the lens.

* * * * *